United States Patent [19]
Castora

[11] Patent Number: 5,947,296
[45] Date of Patent: Sep. 7, 1999

[54] MULTIPACK PACKAGE

[75] Inventor: Valarie M. Castora, Queensburg, N.Y.

[73] Assignee: Schneider/Namic, Glens Falls, N.Y.

[21] Appl. No.: 08/961,172

[22] Filed: Oct. 30, 1997

[51] Int. Cl.⁶ ............................................. B65D 85/20
[52] U.S. Cl. ................... 206/571; 206/364; 206/438; 206/466
[58] Field of Search ............................. 206/363, 364, 206/370, 438, 439, 461, 466, 484, 484.2, 570, 571, 806, 476–478; 383/37, 38

[56] References Cited

U.S. PATENT DOCUMENTS

| | | | |
|---|---|---|---|
| 3,419,137 | 12/1968 | Walck, III | 206/364 |
| 3,913,562 | 10/1975 | Moore et al. . | |
| 4,306,656 | 12/1981 | Dahlem . | |
| 4,573,576 | 3/1986 | Krol | 206/438 |
| 4,660,721 | 4/1987 | Mykleby . | |
| 4,765,653 | 8/1988 | Fasham et al. . | |
| 4,781,297 | 11/1988 | Abrahamsson et al. . | |
| 4,925,448 | 5/1990 | Bazaral | 206/364 |
| 4,972,657 | 11/1990 | McKee | 383/37 |
| 5,031,762 | 7/1991 | Heacox . | |
| 5,165,540 | 11/1992 | Forney | 206/363 |
| 5,257,692 | 11/1993 | Heacox . | |
| 5,372,254 | 12/1994 | Gross | 206/364 |
| 5,388,699 | 2/1995 | Ratajczak et al. . | |
| 5,472,093 | 12/1995 | Nugent et al. . | |
| 5,501,341 | 3/1996 | Van Es | 206/364 |

*Primary Examiner*—Paul T. Sewell
*Assistant Examiner*—Luan K. Bui
*Attorney, Agent, or Firm*—Crompton, Seager & Tufte, LLC

[57] ABSTRACT

A package for containing medical implements in separate pouches packaged together in a continuous strip. The pouches are spaced from one another along the strip and each is maintained in sterile condition until opened. The pouches can be separated one from the other while maintaining the sterility of each pouch and the opening of one pouch can be attained without breaching the integrity and sterility of the another pouch. Each pouch can be opened independently and stored jointly or singly.

9 Claims, 3 Drawing Sheets

MULTIPACK PACKAGE

BACKGROUND OF THE INVENTION

The present invention relates generally to packaging for medical implements. More particularly, the invention relates to the containment of medical implements in separate sterile pouches packaged together in a continuous strip. This configuration allows for the opening of one pouch without breaching the integrity of another pouch. The pouches can be stored in the original or attached configuration or separated and stored separately.

Historically, there have been multipack packages on the market for the storage of medical products. As an example of such product is an angiographic catheter tri-pack which includes left coronary, right coronary and pigtail catheters, the three catheters typically used in an angiographic procedure.

More recently, medical devices for angiographic use, such as the tri-pack package mentioned above, along with a catheter introducer sheath and an angiographic guidewire, have been packaged as a multipack kit. However, there are inherent disadvantages of the kit configurations currently being marketed. The disadvantages primarily center around the lack of flexibility to a user of the devices. The components of an angiographic multipack are typically packaged together in one sterile package. This configuration would be acceptable in cases where all products were to be used in the same procedure. There are times, however, where this may not be the case. If any of the products were not used in that particular procedure, the products not used would likely be discarded as unsuitable because they would be non-sterile once the package was opened. There is yet another packaged medical device product being marketed in which sterile barriers are maintained by fastening two pouches together with a type of cardboard shroud but deficiencies exist, such as, the use of excess of packaging material and the inconvenience of storage.

The foregoing packages all have disadvantages which are overcome through the teachings of the present invention. Specifically, the present invention presents an improved package for medical implements which provides improvements to presently available packages. Thus in accordance with the multipack packaging of the present invention, particularly in regard to packaging for angiography procedures, by separating the catheters and guidewire combination from the sheath in distinct sterile compartments, the contents of one of the compartments can be used without sacrificing the sterility and usefulness of the contents of the other compartment. This is accomplished by means of the integral pouch packaging of the present invention. By way of example, if a physician chooses to use the catheters and guidewire contained in one compartment of the packaging of the present invention, but for some reason chooses not to use the sheath contained in another compartment of the packaging of the invention (perhaps deciding a different size sheath was preferred), the physician can open the compartment containing the catheters and guidewire and leave the sheath in its sterile pouch. This would allow the sheath pouch to be separated and put back into storage for use at a later date. This would not be possible with known packaged medical products.

The multipack packaging of the present invention offers the ability to maintain separate sterile barriers between the products but does so in a way that keeps the package as an integral item. This is accomplished during the pouch manufacturing process by running continuous seals along the length of the pouches and sealing between pouches. The pouches may be of different lengths creating separate compartments for the catheters and guidewire (a relatively long length) and the sheath (a shorter length). Spacing is maintained between the compartments with preferably a perforation and a seal on either side of the perforation within the spacing. Additionally, holes may be punched on either side of the perforation in the non-sealed areas.

A configuration with perforations or scoring allows a user to fold two adjacent compartments together at the weakened section. In a configuration with holes, the holes are punched to line up when the package is folded so that the package can be conveniently hung on a rack. A user may also choose to separate the pouches at a perforation and store the products separately which allows the products to be used in any combination the user wishes without regard for breaking the sterile barrier of the unused product.

SUMMARY OF THE INVENTION

The present invention is directed toward a package for medical implements comprising first and second substantially coextensive layers of material each having first and second longitudinal and transverse edges with the layers being sealed together about the edges and includes first and second transverse margins being spaced from each other and being disposed intermediate the first and the second transverse edges, with the transverse margins each creating a seal joining the layers together to form first and second sealed pouches each adapted to contain at least one medical implement.

Preferably, the package is sized and configured to contain an introducer sheath and a dilator in one of the pouches while the other pouch might contain one or more catheters. One of the pouches might further include an introducer wire. More preferably, the other pouch, in addition to one or more catheters, might further include at least one guidewire.

The package, preferably, includes a card for mounting one of more catheters on one side of the card and, most preferably, for also mounting the guidewire on the opposite side of the card. In one embodiment, the guidewire is surrounded by or enclosed within a tube.

Guidewire mounting and orienting can be achieved by the use of one or more tabs, flaps and clips coacting to retain and position the guidewire. A sleeve is preferably included and may be sized and configured to assist in guidewire retention and positioning.

The package, preferably, further provides for pouch separation while maintaining the integrity of each pouch. Pouch separation might be achieved either by a transverse scoring of the layers between the margins or by a transverse perforating of the layers between the margins. The package might preferably further include openings located between the margins and adapted for storing the pouches either separately or jointly.

The invention further embodies a package for medical implements comprising a first layer having first and second longitudinal edges and first and second transverse edges, a second layer having first and second longitudinal edges and first and second transverse edges, with the layers being superimposed one on the other and being sealed together about the edges, at least two transverse margins being spaced from each other and being disposed intermediate the transverse edges, with the transverse margins each creating a seal joining the layers together along the margins to form first and second sealed pouches each adapted to contain at least one medical implement.

The invention still further embodies a package for medical implements comprising a first end portion and a second end portion, with the first and second end portions being separated by an intermediate portion, with the first end portion being sealed about its periphery to form a first pouch, and with the second end portion being sealed about its periphery to form a second pouch, with one of the pouches being adapted to receive an introducer sheath and a dilator and with the other of the pouches being adapted to receive a catheter. In a preferred embodiment, one of the pouches is further adapted to receive a guidewire.

In yet another embodiment the invention embraces an angiography kit comprising a first portion and a second portion, with the first and second portion being separated by an intermediate portion, with the first portion being sealed about its periphery to form a first pouch, and with the second portion being sealed about its periphery to form a second pouch, with one of the pouches being adapted to receive an introducer sheath and a dilator and the other pouch being adapted to receive more than one catheter and a guidewire. Preferably, the catheters are at least one left coronary, one right coronary and one pigtail catheter.

In still another embodiment, the invention includes an angiography kit comprising a first portion and a second portion, with the first and second portion being separated by an intermediate portion, the first portion being sealed about its periphery to form a first pouch, the second portion being sealed about its periphery to form a second pouch, with one of the first and the second pouch being adapted to receive an introducer sheath and a dilator and with the other of the first and second pouch being adapted to receive a plurality of catheters mounted on a first side of a card and a guidewire mounted of a second side of the card. Preferably, the plurality of catheters includes left coronary, right coronary and pigtail catheters.

DETAILED DESCRIPTION OF THE PREFERRED EMBODIMENTS

Figure 1:
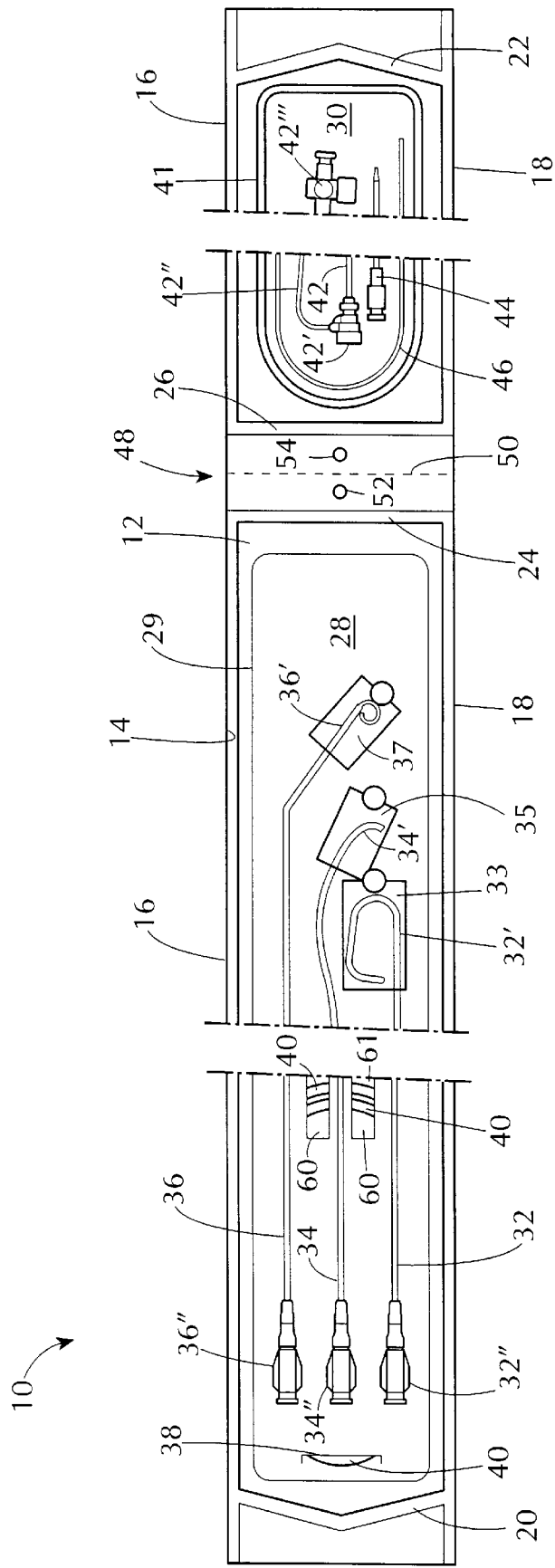
FIG. 1 is a schematic, partial, top plan view of an embodiment of a multipack package in accordance with the principles of the present invention and, in a first pouch, illustrating an angiographic catheter tri-pack of left coronary, right coronary and pigtail catheters and, in a second pouch, illustrating a catheter introducer sheath, a dilator and an introducer wire.

The description herein presented refers to the accompanying drawings in which like reference numerals refer to like parts throughout the several views. Referring to FIG. 1, in accordance with the principles of the present invention, there is illustrated a schematic, perspective, partial (shortened) view of a first embodiment of a multipack medical package 10. The package 10 includes a first layer 12 (top) and a second layer 14 (bottom), with the layers being substantially coextensive, having longitudinal edges 16 and 18 and having transverse edges 20 and 22. Package 10 further includes first and second transverse margins 24 and 26. Layer 12 is preferably a laminate of polyethylene and polyester and layer 14 is preferably spun bonded polyolefin. Layers 12 and 14 are heat and pressure sealed ill a conventional manner about longitudinal edges 16 and 18, transverse edges 20 and 22 and margins 24 and 26 to form first and second pouches 28 and 30 to contain at least one medical implement in each pouch.

Left coronary catheter 32, right coronary catheter 34, pigtail catheter 36 and guidewire 56 are included in pouch 28 and are mounted on a card 29. Ends 32', 34' and 36' of the catheters are contained within shape retaining pouches 33, 35 and 37. Additionally shown are catheter hubs 32", 34" and 36" and slit or slot 38 cut in mounting card 29. It should be understood that, while shape retaining pouches 33, 35 and 37 are depicted in this view, there may be some instances where catheters are packaged in a multipack package of the present invention but such catheters will not necessarily include shape retaining pouches. Tube 40, which houses a guidewire (not shown in this view) on the opposite side of card 29, can be seen both at the slot location and in openings 61. Pouch 30 includes a tray 41 containing an introducer sheath 42 having a hub 42', a side arm 42" and a stopcock 42''', a dilator 44 and an introducer wire 46. It should be understood that included within the scope of the invention is any medical appliance or implement suitable for packaging in a sterile pouch.

The package preferably further includes an intermediate zone or portion 48 located between margins 24 and 26, and includes either a perforation or a scoring line 50 or equivalent in the intermediate zone or portion 48 to assist a user in separating pouch 28 from pouch 30 by tearing the package along line 50. Also preferably there is included openings 52 and 54 in the intermediate zone or portion 48. The openings allow for storage of either of pouches 28 or 30 singly or the storage of the pouches jointly. Pouches 28 and 30 can be separated along line 50 for use of either pouch or for storage of either pouch. The package can be folded along line 50 to align openings 52 and 54 for hanging both of the pouches together. It should be understood that the pouches are sterilized in a conventional manner such as by using ethylene oxide gas and that the opening of one pouch will not disturb the sterile integrity of the other pouch. It should be understood that within the scope of the invention is the inclusion in the pouches of some but not necessarily all of the items depicted in FIG. 1.

Figure 2:
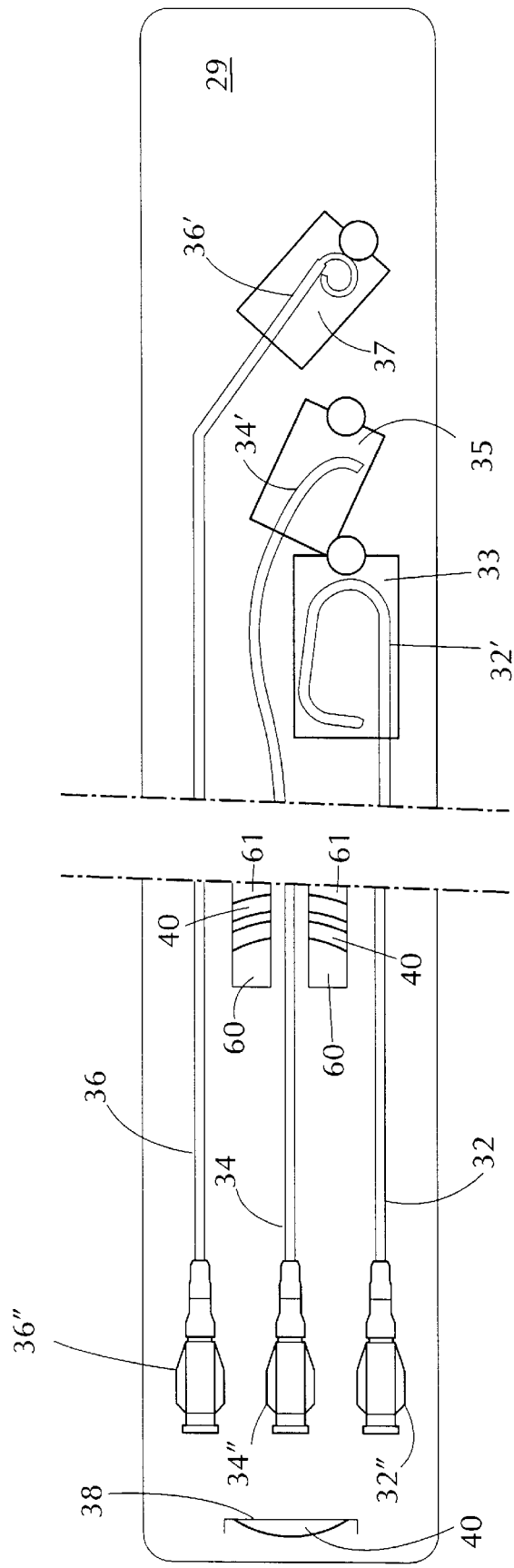
FIG. 2 is an enlarged, schematic, top plan view of the contents of the left pouch shown in FIG. 1 depicting the catheters mounted on a card.

Turning to FIG. 2, there is shown more clearly the contents of pouch 28 which includes mounting card 29 upon which there is mounted on one side catheters 32, 34 and 36. Also shown is a portion of tube 40 contained in slit or slot 38 and in openings 61.

Figure 5:
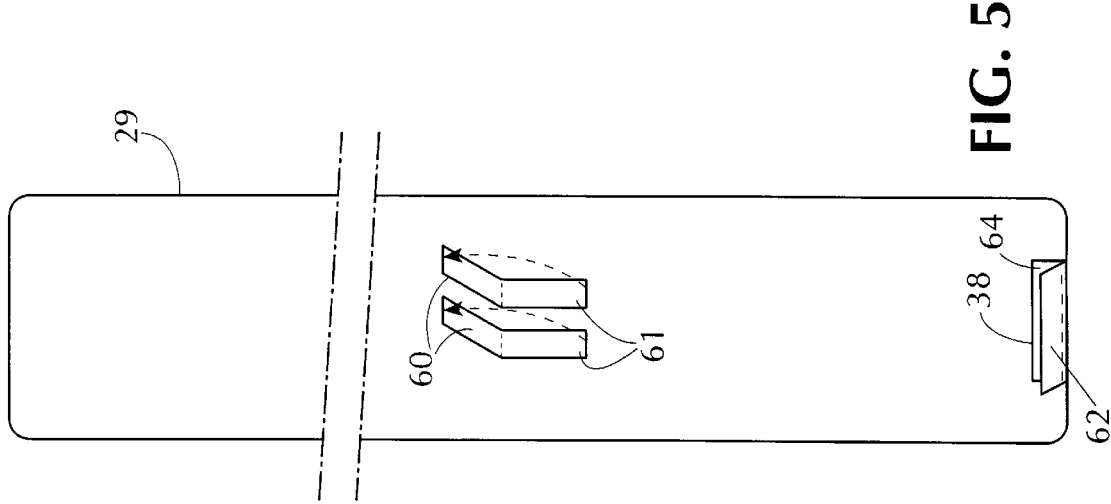
FIG. 5 is a bottom plan view of the mounting card depicted in FIG. 4 without inclusion of a guidewire mounted thereon.
Figure 4:
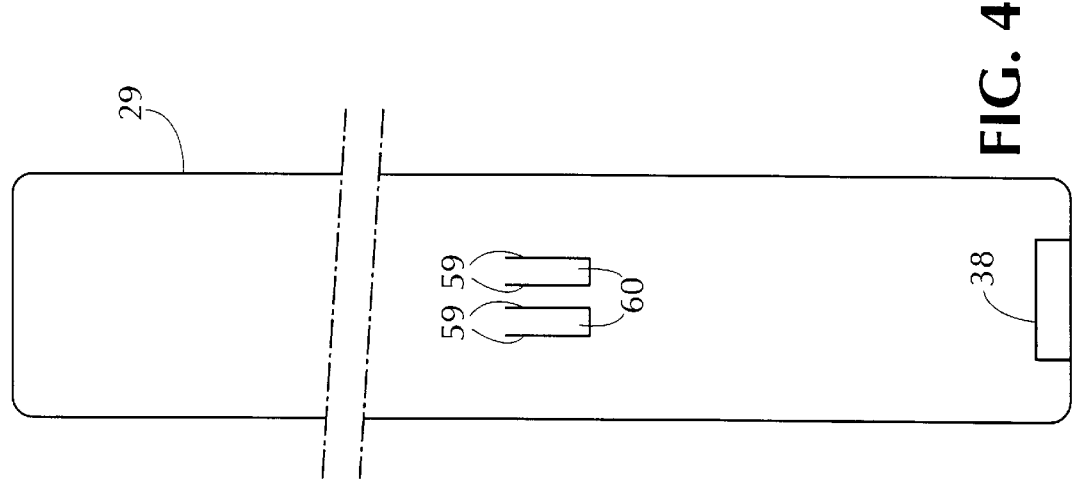
FIG. 4 is a reduced, top plan view of the mounting card depicted in FIG. 2 but without the catheters mounted thereon.
Figure 3:
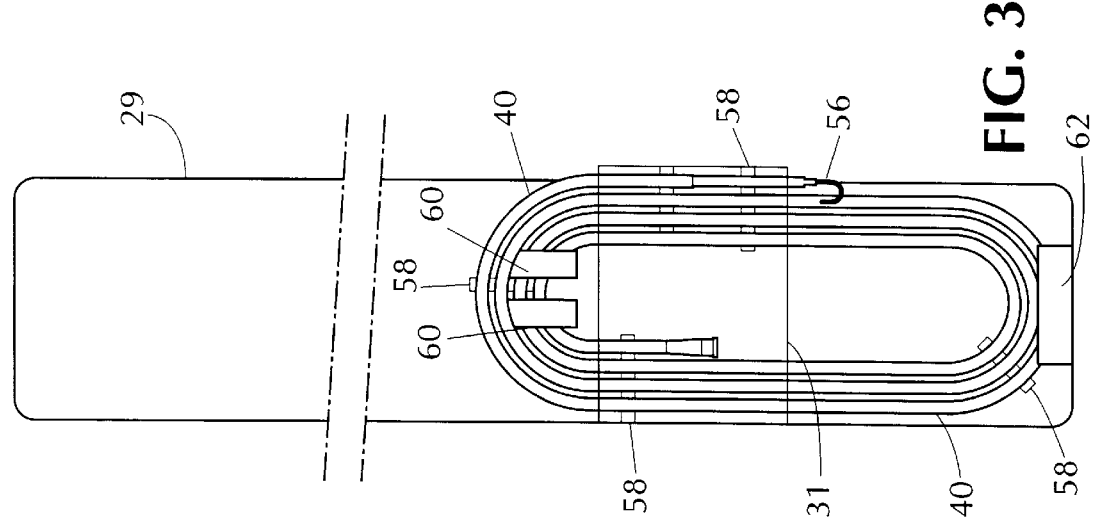
FIG. 3 is a reduced, bottom plan view of the card depicted in FIG. 2 showing a guidewire mounted on the card.

Turning to FIG. 3 there is shown the other side of card 29 upon which there is mounted tube 40 containing a guidewire 56. It should be understood that the guidewire could be mounted without the tube but preferably tubing is used. The combination of tube 40 containing guidewire 56 is coupled to card 29 by tabs 60 and flap 62. Preferably, also included is a sleeve or band 31 which is sized and configured to enclose at least a portion of the tube containing the guidewire and serves to maintain the tube/guidewire in a predetermined orientation. Further included might be clips 58 which are used to maintain a predetermined orientation or position of the tube/guidewire mounted to the card. The tabs 60 are preferably formed in card 29 as can be best seen in FIGS. 4–5. The tabs 60 are formed by cutting slits 59 in card 29 (FIG. 4) and bending the tabs (FIG. 5) creating opening 61. In FIG. 4 there is shown slit 38 which upon bending creates a flap 62 (FIG. 5) and forms opening 64. The tube 40 and guidewire 56 are coupled to card 29 by bending at least a portion of tabs 60 over the tube and guidewire (FIG. 3). Optionally, the end of each tab may be fastened to the card such as with tape or the like. For additionally securing the tube and guidewire, or the tube or guidewire solely, the tube/guidewire can be located in opening 64 and the flap 62 can be pressed against the tube/guidewire.

I claims:

1. A package for medical implements comprising first and second substantially coextensive layers of materials each having first and second longitudinal and transverse edges, said layers being sealed together about said edges, first and second transverse margins being spaced from each other and being disposed intermediate said first and said second transverse edges, with said transverse margins each creating a seal joining said layers together to form first and second sealed pouches;

wherein at least one of said first and second pouches contains a card including means for holding packaged items;

wherein one of said first and second pouches contains an introducer sheath and a dilator; and the other of said first and second pouches contains at least one catheter.

2. The package according to claim 1 wherein the other of said first and second pouches further includes at least one guidewire.

3. A package for medical implements comprising first and second substantially coextensive layers of materials each having first and second longitudinal and transverse edges, said layers being sealed together about said edges, first and second transverse margins being spaced from each other and being disposed intermediate said first and said second transverse edges, with said transverse margins each creating a seal joining said layers together to form first and second sealed pouches;

wherein at least one of said first and second pouches contains a card including means for holding packaged items;

wherein one of said first and second pouches contains an introducer sheath and a dilator; and the other of said first and second pouches contains a card and at least one catheter mounted on a first side of said card.

4. A package for medical implements, comprising;

first and second substantially co-extensive layers of materials each having first and second longitudinal and transverse edges, said layers being sealed together about said edges;

first and second transverse margins being spaced from each other and being disposed intermediate said first and second transverse edges, with said transverse margins each creating a seal joining said layers together to form first and second sealed pouches;

wherein one of said first and second pouches contains an introducer sheath and a dilator;

wherein the other of said first and second pouches contains a card and at least one catheter mounted on a first side of said card; and said package further including at least one guidewire and means for mounting said guidewire on a second side of said card.

5. The package according to claim 4 wherein said means is at least one tab coupling said guidewire to said card.

6. The package according to claim 5 wherein said means further includes at least one flap coupling said guidewire to said card.

7. The package according to claim 4 further including a sleeve sized and configured to enclose at least a portion of said guidewire to maintain said guidewire in a predetermined orientation.

8. The package according to claim 4 further including one or more clips to maintain said guidewire in a predetermined orientation.

9. The package according to claim 4 further including a tube surrounding said guidewire.

* * * * *